US005528034A

United States Patent [19]
Yamazaki et al.

[11] Patent Number: 5,528,034
[45] Date of Patent: Jun. 18, 1996

[54] METHOD OF ULTRA HIGH SENSITIVITY HYDROGEN DETECTION WITH SLOW MULTIPLY-CHARGED IONS

[75] Inventors: Yasunori Yamazaki, Machida; Kenichiro Komaki, Kawasaki; Toshiyuki Azuma; Nobukazu Kakutani, both of Tokyo; Kenro Kuroki, Urawa, all of Japan

[73] Assignee: The University of Tokyo, Tokyo, Japan

[21] Appl. No.: 411,992

[22] Filed: Mar. 28, 1995

[30] Foreign Application Priority Data

Sep. 28, 1994 [JP] Japan ................................. 6-233549

[51] Int. Cl.⁶ ........................ H01J 37/252; G01N 23/225
[52] U.S. Cl. ............................................ 250/309; 250/288
[58] Field of Search ................................. 250/309, 288

[56] References Cited

U.S. PATENT DOCUMENTS 3,920,989  11/1975  Erickson et al. ..................... 250/309
4,352,985  10/1982  Martin .................................. 250/309

OTHER PUBLICATIONS

Clark et al., Applied Physics Letters, vol. 31, No. 9, 1 Nov. 1977, pp. 582–585.

*Primary Examiner*—Jack I. Berman
*Attorney, Agent, or Firm*—Sughrue, Mion, Zinn, Macpeak & Seas

[57] ABSTRACT

The present invention is to provide a method for detecting hydrogen with ultra high sensitivity based on slow multiply-charged ion wherein damages of a target surface can be remarkably reduced and a quantitative analysis of hydrogen atoms on a solid surface can be compactly realized with extremely high efficiency by employing slow multiply-charged ions derived from an ion source for efficiently generating multiply-charged ions. The present invention relate to a method of ultra high sensitivity hydrogen detection based on slow multiply-charged ions comprising: arranging an EBIS type slow multiply-charged ion source for generating slow multiply-charged ions having potential energy higher than kinetic energy, a Wien filter type mass analyzer, a deflector for producing a pulsed ion beam, an acceleration ring provided with apertures lenses and a secondary ion detector, a target on a Cu mesh provided on the acceleration ring and a secondary electron multiplier in order on a beam line for carrying ions from the ion source, detecting secondary ions generated upon the collision of slow multiply-charged ions with the target by accelerating the secondary ions toward the secondary ion detector, detecting secondary electrons in the secondary electron multiplier by repelling toward the mesh target and measuring a time difference between a secondary electron detection time on the secondary electron multiplier and a secondary ion detection time on the secondary ion detector, thereby effecting a quantitative analysis of hydrogen atoms on a solid surface of the target on the Cu mesh.

2 Claims, 13 Drawing Sheets

FIG_1
PRIOR ART

FIG_5

FIG_8A

FIG_8B

FIG_9

FIG. 10

FIG_11

METHOD OF ULTRA HIGH SENSITIVITY HYDROGEN DETECTION WITH SLOW MULTIPLY-CHARGED IONS

BACKGROUND OF THE INVENTION

1. Field of the Invention

The present invention relates to a method of ultra high sensitivity hydrogen detection in which, on the basis of slow multiply-charged ions from an ion source for efficiently generating multiply-charged ions such as an electron beam ion source (EBIS) or an electron cyclotron resonance ion source (ECRIS), damages caused on a target surface can be remarkably reduced and a quantitative analysis of hydrogen on a solid surface can be compactly realized with extremely high efficiency.

2. Description of the Related Art

The quantitative analysis of hydrogen on the solid surface and in the solid has been conventionally very difficult. As for the detection of hydrogen on the solid surface or in the solid, a method in which resonant nuclear reaction with nitrogen can be cited. In this method, the depth resolution estimated as the order of a few atom layers strongly depends on the energy resolution of an accelerator.

In the resonant nuclear reaction, nitrogen ions accelerated to a few MeV are necessitated and a phenomenon which acts as a probe is a nuclear reaction, so that the detection efficiency is very low and hence requires several hours, and further it is naturally required to provide an ion accelerator of middle size.

Figure 1:
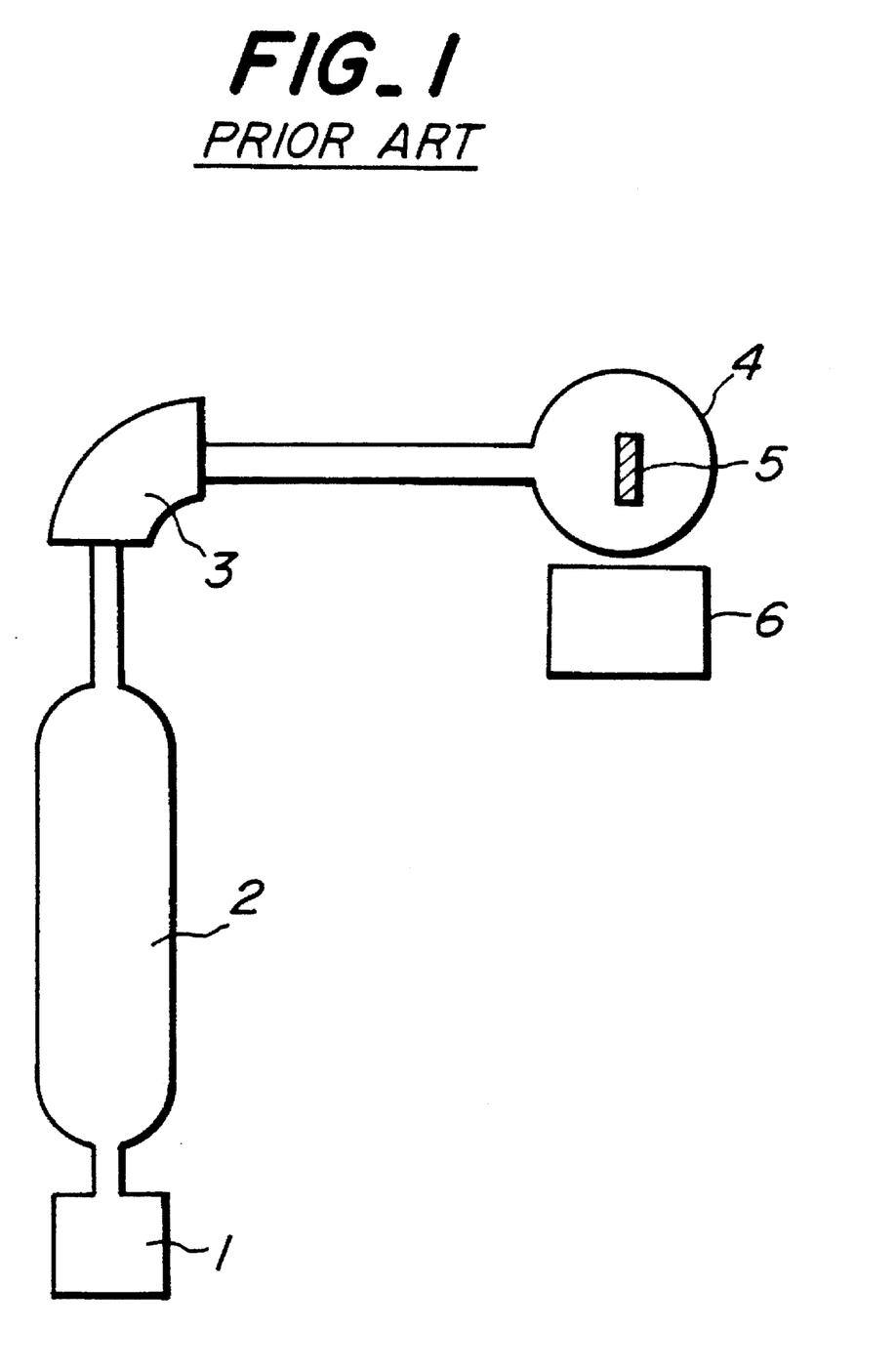
FIG. 1 is a schematic diagram to detect hydrogen with a conventional method which employs a nuclear resonant reaction.

An outlined arrangement provided for the conventional method of hydrogen detection is shown in FIG. 1. In FIG. 1, 1 denotes a negative ion source, ions extracted from the negative ion source are accelerated and charge-stripped by a tandem accelerator 2 and charge-state-analyzed by an analyzing magnet 3 and then transported to a target 5 which is set in an experimental vacuum chamber 4, where γ-rays emitted from the target 5 are detected by a γ-ray detector 6.

As mentioned above, the conventional method of surface hydrogen detection is large-scaled and has low detection efficiency and further has a serious defect in the sense that the target surface is strongly damaged by the collision of the probe ions.

In addition, atoms on the solid surface which are heavier than hydrogen, for instance, Li-atoms, have been conventionally detected through Auger electron spectroscopy which has a particularly high sensitivity in the vicinity of the solid surface. However, hydrogen atoms don't emit Auger electrons and hence form a blind spot of the conventional method of surface atom detection.

SUMMARY OF THE INVENTION

The present invention is to obviate afore-mentioned shortcomings providing a method of ultra high sensitivity hydrogen detection from which the afore-mentioned various defects are removed on the basis of a recognition that the quantitative analysis of hydrogen atoms on a solid surface can be compactly realized with extremely high efficiency by employing slow multiply-charged ions which are efficiently produced by an electron beam ion source (EBIS) or an ECR ion source (ECRIS).

An object of the present invention is to provide a method of ultra high sensitivity hydrogen detection employing slow multiply-charged ions comprising: (i) an EBS type ion source to supply slow multiply-charged ions having potential energy larger than kinetic energy, (ii) a Wien filter type mass analyzer, (iii) a deflector to which is applied a periodic square wave voltage to make a pulsed ion beam, (iv) a secondary ion analyzer consisting of apertures, electrostatic lenses, and a microchannel plate for secondary ion detection, (v) a target on a Cu mesh, and (vi) a channeltron to detect secondary electrons from the target. When a multiply-charged ion hits the target, secondary ion(s) and secondary electron(s) are emitted. The difference of detection times between the secondary electron and the secondary ion which belong to the same incident ion gives the charge to mass ratio of the secondary ion, which enables quantitative analysis of hydrogen atoms on a solid surface.

The EBIS type multiply-charged ion source employed by the present invention comprises an electron gun, a drift tube, a solenoid coil coaxially surrounding the drift tube, four iron bars surrounding the solenoid coil and an electron collector outside of the drift tube, so as to obtain a high density electron beam by magnetically shielding input and output sides of the drift tube through a W-metal and a soft iron pipe respectively for generating an intense magnetic field in the direction of the drift tube axis.

The whole set-up of the present hydrogen atom detection system comprises:

(1) an ion source for supplying slow multiply-charged ions such as an electron beam ion source (EBIS) or an electron cyclostron resonance ion source (ECRIS);

(2) a beam line for transporting ions from the ion source to the target area;

(3) an ultra high vacuum chamber to set a sample to be analyzed; and (4) a mass analyzer for detecting hydrogen ions released from a solid surface.

BRIEF DESCRIPTION OF THE DRAWINGS

For the better understanding of the invention, reference is made to the accompanying drawings, in which.

Through different views of the drawings: 1 is a negative ion source, 2 is a tandem accelerator, 3 is an analyzing magnet, 4 is an experimental vacuum chamber, 5 is a target, 6 is a γ-ray detector for monitoring resonant nuclear reaction, 11 is an electron beam ion source, 12 is an ion beam, 12A is a secondary ion, 12B is a secondary electron, 13 is a Wien filter type mass analyzer, 14 is a deflector, 14A is an AC voltage supply, 15 is an aperture, 16 is an electrostatic lens, 17 is a micro-channel plate (MCP) for secondary ion detection, 18 is a secondary ion acceleration ring, 19 is a target, 20 is a secondary electron multiplier, 21 is an ultra high vacuum chamber for the EBIS, 24 is an electron gun consisting of a cathode 22 and an anode 23, 25A, 25B are soft iron tubes, 26A, 26B are μ-metals, 27 is an ion beam, 28 is a drift tube, 29 is a solenoid coil, 30 are iron bars, 31 is an electron collector, 32 is an ion lens system, 33 is a liquid nitrogen cryostat, 34 is a vacuum pump, 35 is a valve to control liquid nitrogen, 37, 38 are slits.

DESCRIPTION OF THE PREFERRED EMBODIMENT

Preferred embodiments will be described in detail hereinafter by referring to the accompanying drawings.

Figure 2:
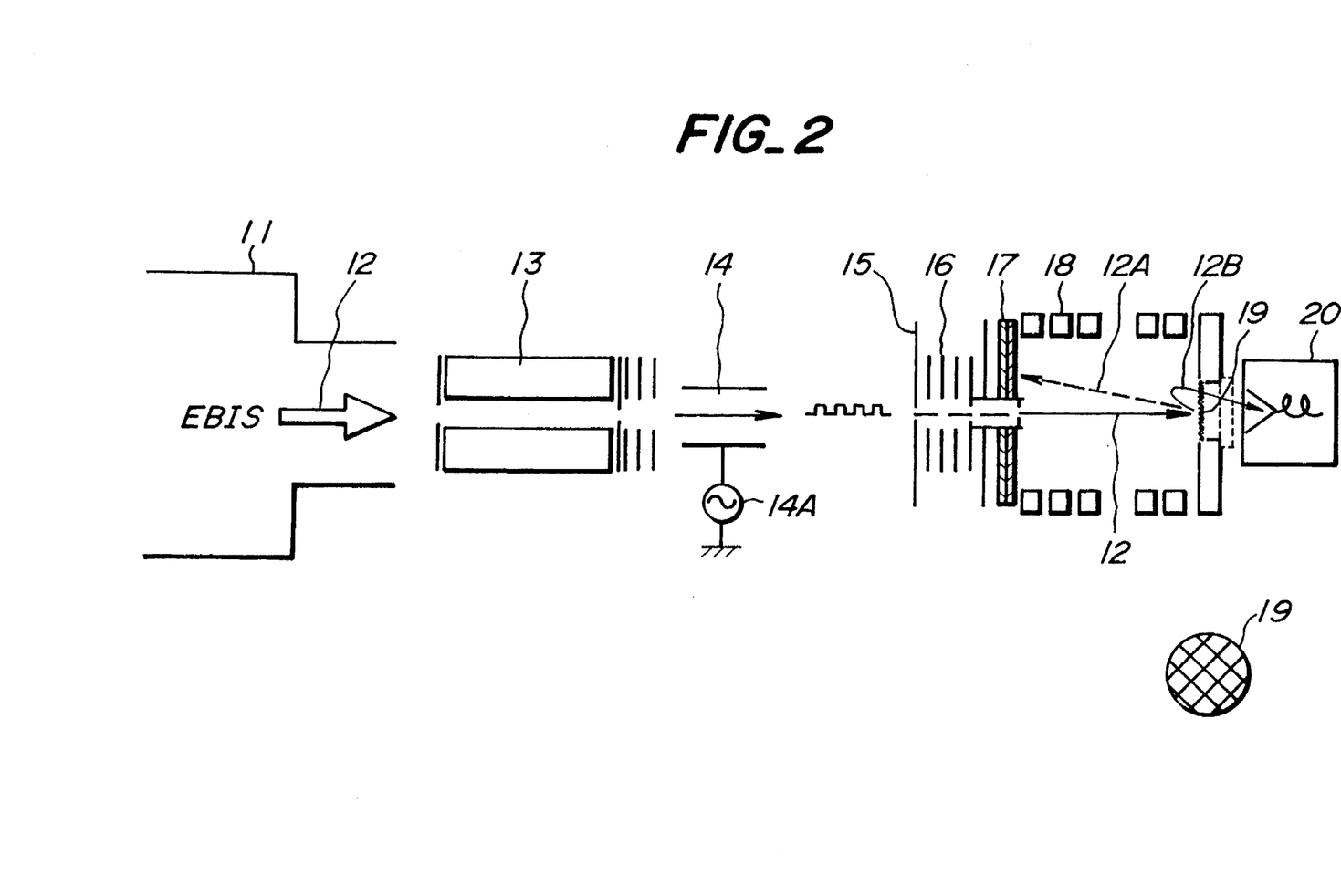
FIG. 2 is a diagram showing the hydrogen detection arrangement employed in the present invention.

As shown in FIG. 2, a beam line for transporting ions extracted from an EBIS type ion source 11 is constructed with a Wien filter type mass analyzer 13, a deflector 14, apertures 15, lenses 16, a micro-channel plate (a secondary ion detector) 17, an acceleration ring 18, a target and a secondary electron multiplier 20. 14A is an AC voltage supply connected to the deflector 14 for reforming the ion beam into a series of pulses. The ion source 11, the mass analyzer 13, the deflector 14, the apertures 15, the lenses 16, the acceleration ring 18 and the secondary electron multiplier 20 are all installed in an ultra high vacuum system.

Figure 3:
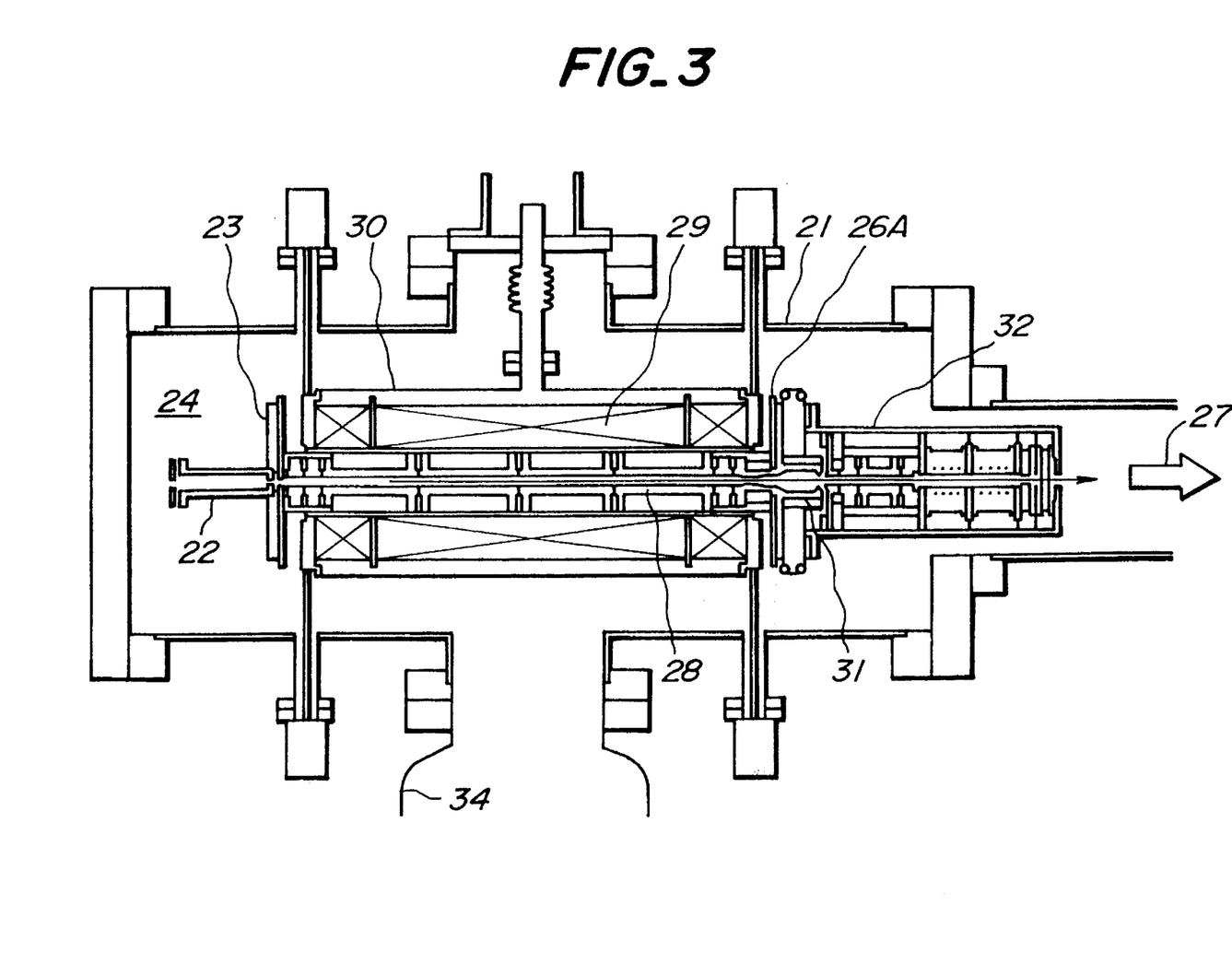
FIG. 3 is a sectional view of the electron beam ion source (EBIS) used in the present invention.

FIG. 3 shows an example of the EBIS (Electron Beam Ion Source) type slow multiply-charged ion source employed in the present invention.

In FIG. 3, electrons emitted from an electron gun 24 installed in one end of an ultra high vacuum chamber 21 where magnetic field of the solenoid is shielded by a soft iron tube 25A and a μ-metal 26A pass through a drift tube 28 which is surrounded by a solenoid coil 29 and iron bars 30, and then are collected by an electron collector 31, which is followed by an ion lens system 32.

Figure 4:
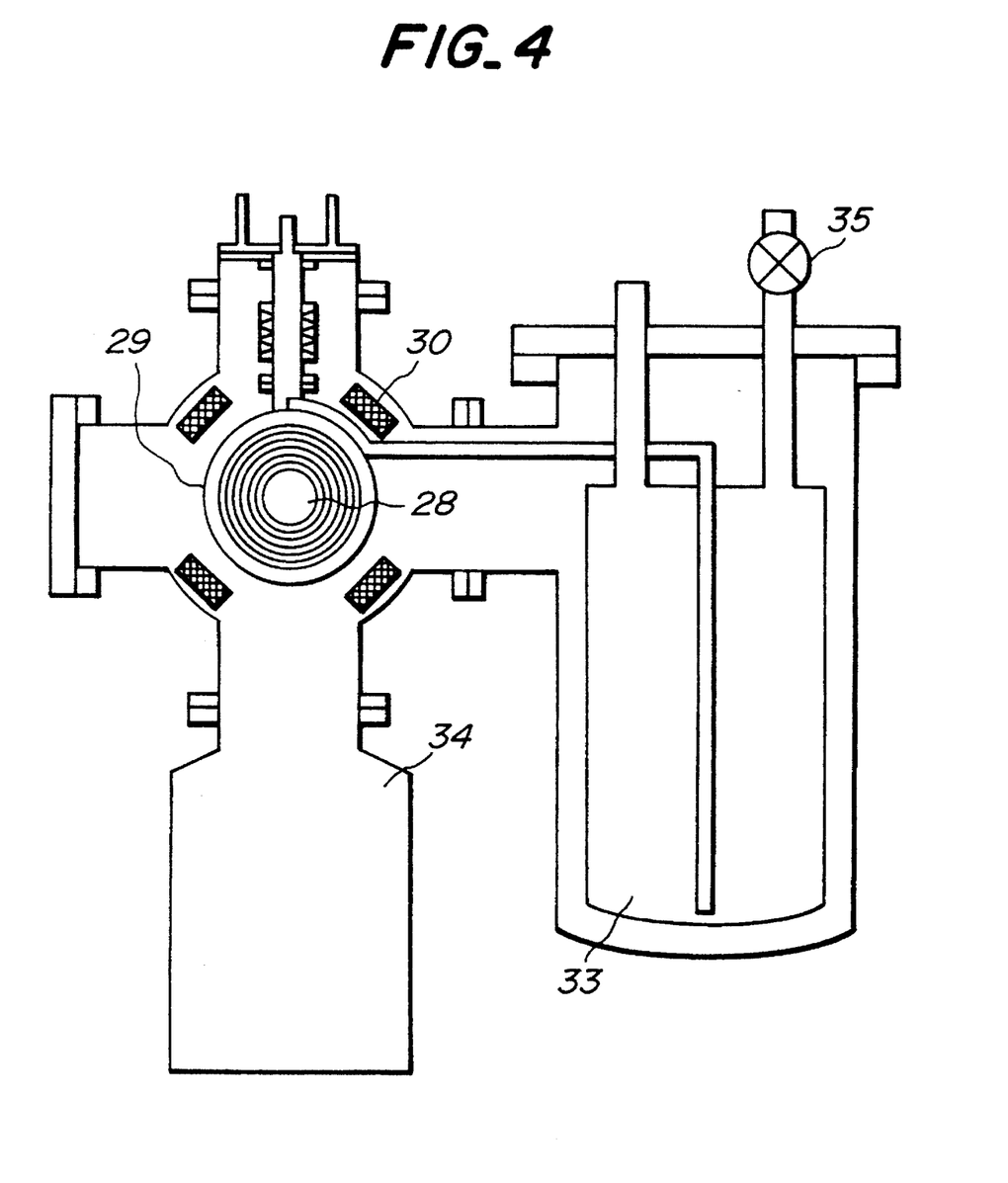
FIG. 4 is a crosssectional view of the EBIS including a liquid nitrogen cryostat and a vacuum pump.

FIG. 4 shows an elevational crosssectional view of the ion source shown in FIG. 3. In FIG. 4, 35 denotes a valve to control the flow of liquid nitrogen from the cryostat 32 to the solenoid 29. A turbo molecule pump 34 maintains the vacuum chamber in an ultra high vacuum with an evacuation speed of 300 L/sec.

Figure 5:
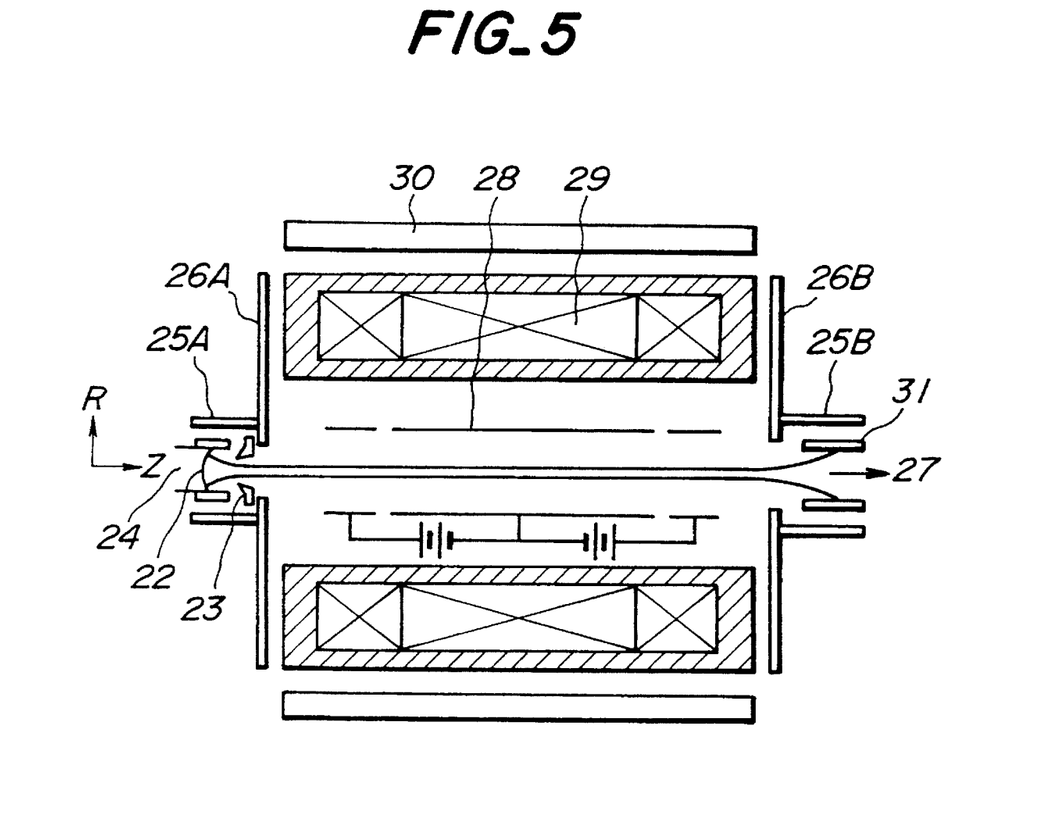
FIG. 5 is a schematic drawing showing the structure of the EBIS as shown in FIG. 3.

FIG. 5 shows a schematic drawing of the ion source. In FIG. 5, electrons emitted from the electron gun 24 comprising the cathode 22 and the anode 23 which is magnetically shielded by the soft iron tube 25A and the μ-metal 26A are carried through the drift tube 28 which are surrounded by the solenoid coil 29 and four iron bars 30, and then collected by the electron collector 31.

Figure 6A:
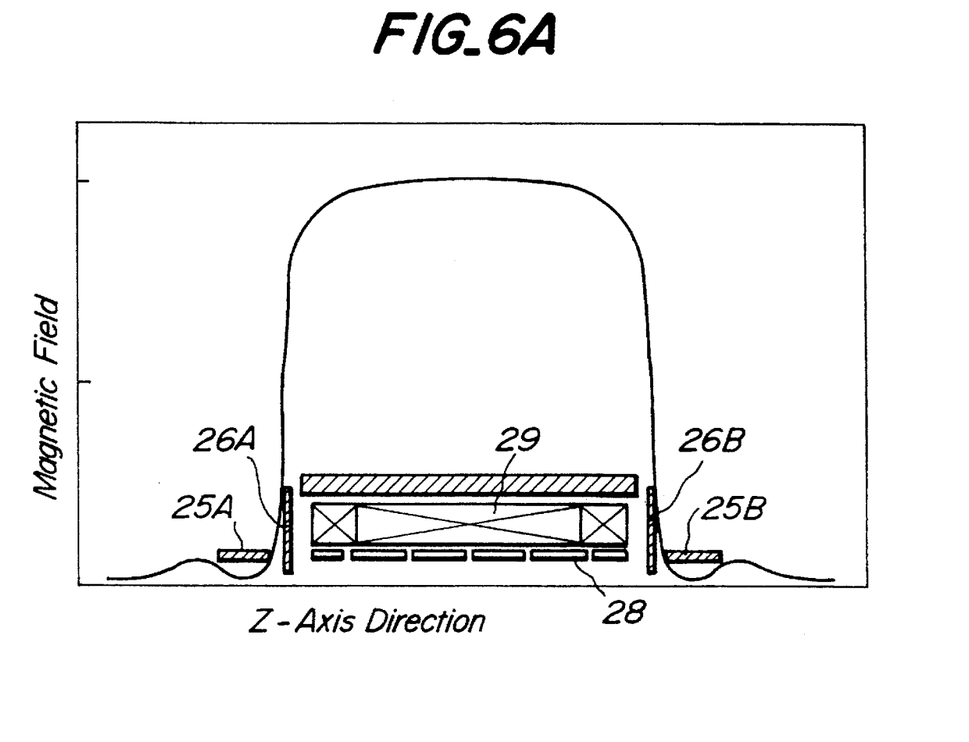
FIG. 6(A) is a sectional diagram showing a schematic distribution of magnetic field along the axis of the solenoid.
Figure 6B:
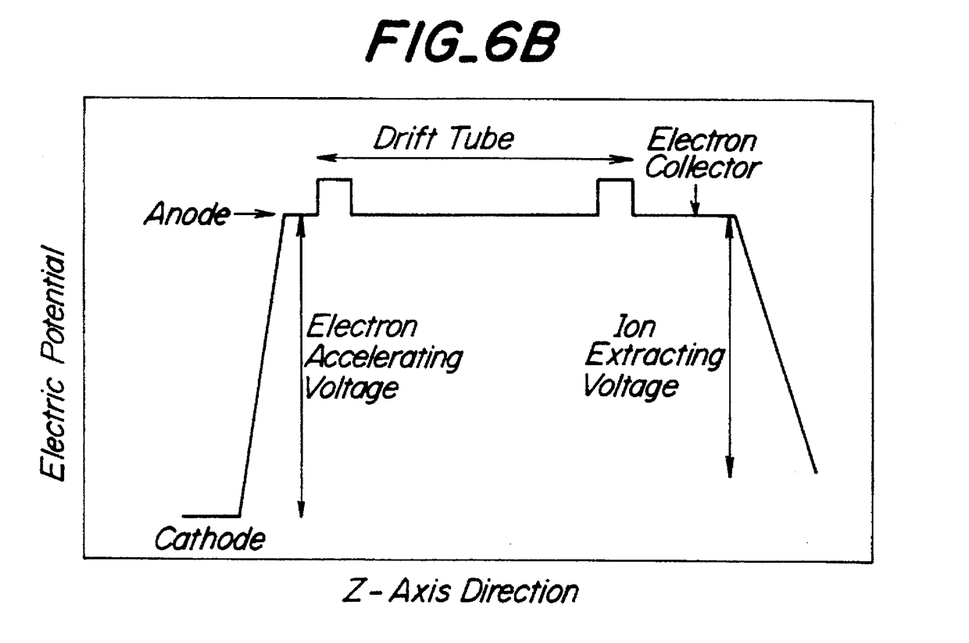
FIG. 6(B) is a schematic drawing of the potential distribution along the drift tube axis.

FIG. 6A shows a schematic distribution of a magnetic field along the central axis of the solenoid coil 29 in the EBIS employed in the present invention. FIG. 6B shows a schematic distribution of an electric potential in the EBIS along the same axis as in FIG. 6A.

Figure 7A:
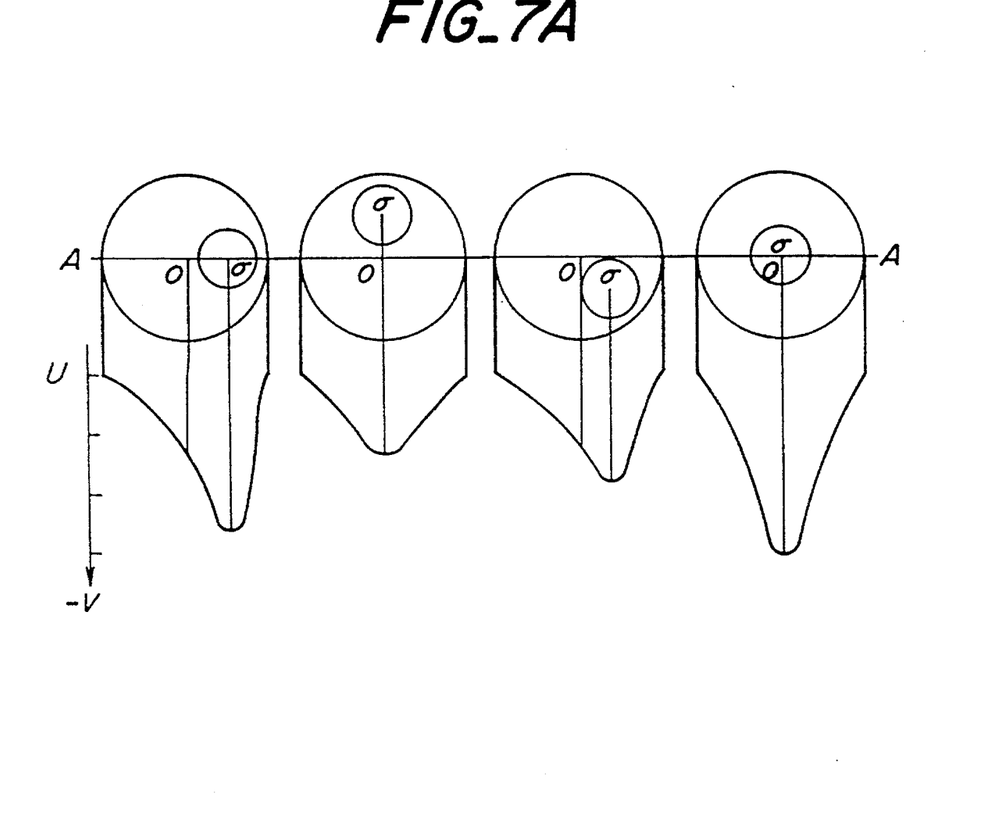
FIG. 7(A) is a diagram showing examples of distribution in the drift tube for various electron beam positions which is denoted by small circles.
Figure 7B:
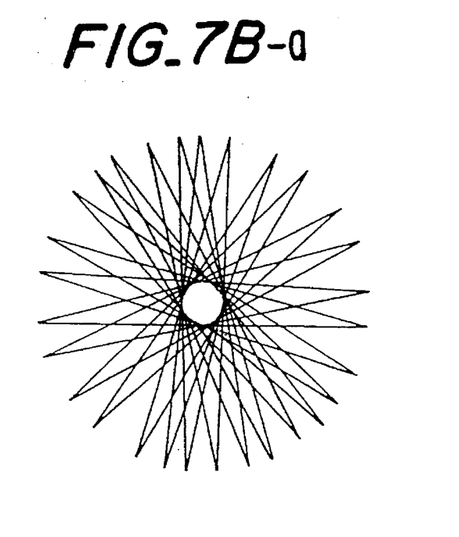
FIG. 7(B) is a diagram showing examples of radial trajectories of ions trapped in the drift tube with electron beam.
Figure 8A:
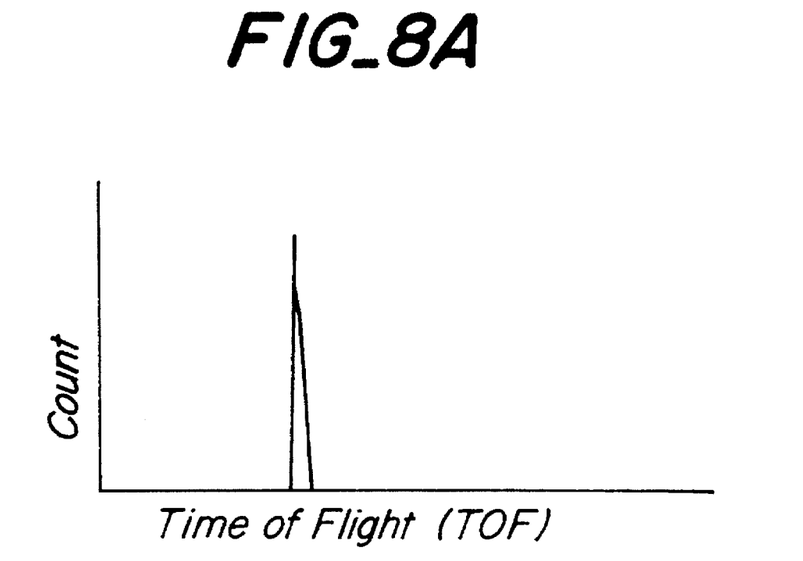
FIGS. 8A and 8B are schematic diagrams showing time of flight (TOF) spectra of secondary ion(s) for (A) one ion and (B) multiple ions emission.
Figure 8B:
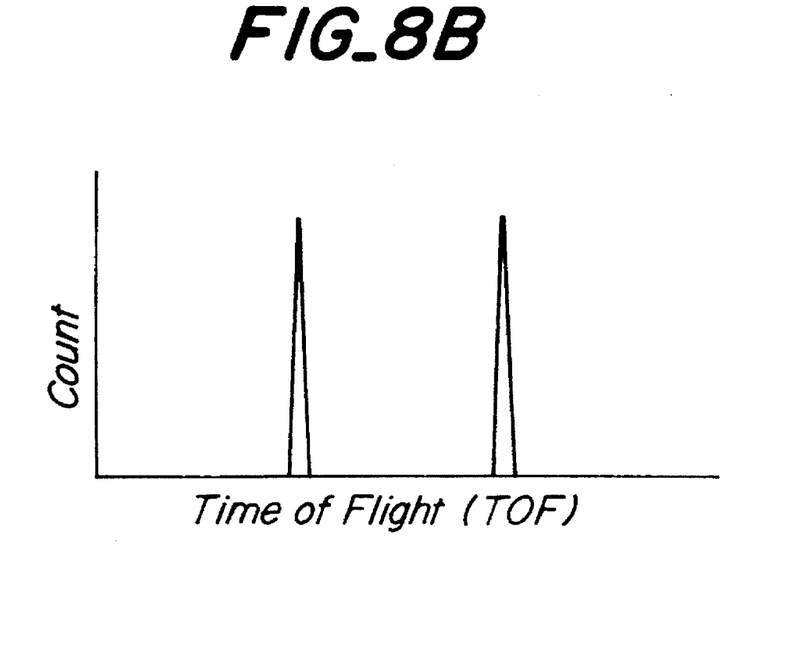

FIG. 7A shows examples of the radial distribution of electric potential in the drift tube 28 of EBIS for several positions of the electron beam 27. FIG. 7B shows examples of radial orbits of ions trapped in the electric potential formed by the electron beam 27 and the drift tube shown in FIG. 7A. FIG. 7(B)-$a$ is a case for $Xe^{8+}$ with its initial kinetic energy zero, the electron beam energy is 50 keV with beam density of $6 \times 10^{11}$ e/cm$^2$, and the magnetic field is 5T, the amplitude of radial direction being 0.01 cm, while FIG. 7(B)-$b$ is a case for the same ion but with initial kinetic energic of 50 eV and with a large angular momentum, the amplitude of radial direction being 0.025 cm.

Multiply-charged ions having potential energy larger than kinetic energy are generally called slow multiply-charged ions. When an ion having charge q approaches a solid surface, plural electrons (>q) are transferred to the incident ion from a capture region near the surface, which charges up strongly. As a result, atoms on the target surface, from which electrons are removed, repel each other by their coulomb interaction and hence are emitted in vacuum as ions. In the present invention, under the attention to hydrogen atoms on a solid surface which are generally regarded as difficult to be detected and identified, it is clarified that the detection efficiency thereof is extremely high for slow multiply-charged ions, and hence a quite novel detection method thereof is proposed.

FIG. 2 schematically shows the principle of the detection method according to the present invention; slow multiply-charged ion beam 12 from the EBIS type ion source 11 is charge-state- and mass-analyzed by the Wien filter type mass analyzer 13 reformed into a pulsed beam at the deflector 14 by the high frequency voltage applied from the AC oscillator 14A. This pulsed beam is successively passed the apertures 15, the lenses 16, the micro-channel plate (MCP 17), and the acceleration ring 18, and finally collides with the target 19 which is prepared on a copper mesh. The secondary ion 12A, which is formed by removing electrons from the target 19 and emitted by mutual Coulomb repulsion, is accelerated through the accelerator 18 toward the MCP 17. The mass to charge ratio of the emitted secondary ion is determined from the time of flight (TOF) to the MCP 17.

Figure 9:
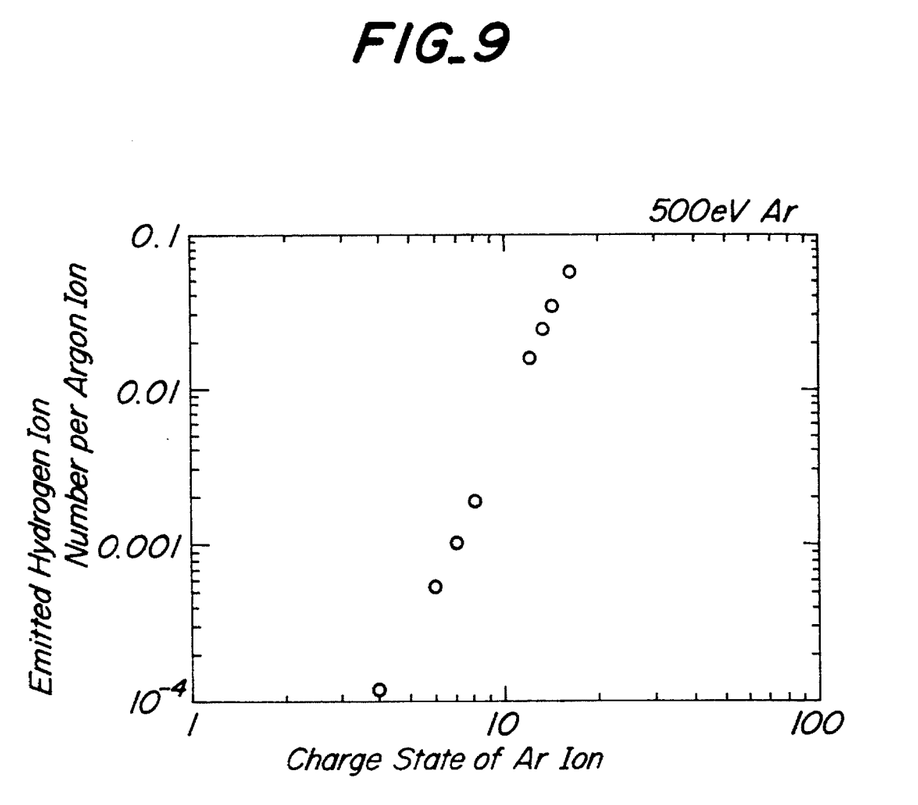
FIG. 9 is a diagram showing a relation of secondary hydrogen ion (proton) yield with respect to charge state for 500 eV Ar ions.

FIG. 9 shows the secondary hydrogen ion (proton) yield as a function of charge state for 500 eV Ar ions. It is seen from FIG. 9 that the observed H$^+$ intensity strongly increases with the charge state of incident ions like q$^4$ and that the absolute yield reaches to extremely large value, for example, one H$^+$ for every 10 injected ions at q=16. Such high detection efficiencies of H$^+$ have never been realized by any detection method other than the present invention.

Slow multiply-charged ions 12 supplied from the EBIS ion source 11 provided on left end in FIG. 2 are charge-state-selected with the Wien filter type mass analyzer 13, and then reformed into a pulsed beam through the deflector 14 applied with oscillating electric field by the AC voltage supply 14A. Thus pulsed ion beam collides onto the target 19 deposited on a copper mesh through the lens 16, the MCP 17 and the acceleration ring 18. From the target 19 struck by the multiply-charged ion beam, secondary ions 12A and secondary electrons 12B are emitted. The acceleration ring 18 is operated in such a way that the secondary ion 12A is accelerated toward the MCP 17 and the secondary electron 12B is repelled toward the mesh target 19. Multiply-charged ions generate plural secondary electrons 12B, a part of which pass through the target mesh 19 and then detected by the secondary electron multiplier 20. Electrons are far lighter than ions and hence readily move, so that, the secondary electrons 12B are detected by the multiplier 20 almost at the same time when the slow multiply-charged ion arrives at the mesh target 19.

In this presently used detection system, the time of flight of the secondary ion 12A between the target 19 and the MCP 17 is measured from the time difference between the detection time of the secondary ion 12A on the MCP 17 and the detection time of the secondary electron 12B on the multiplier 20, so as to identify the kind of the secondary ion. That is, the mass m of secondary ion can be defined from the following equation, $$m = qVt^2/2L^2$$

where q is the electric charge of the secondary ion, L is the distance between the target 19 and the MCP 17 and V is the voltage applied between the target 19 and the MCP 17. It is usually set that V=2 kV in order to increase the detection efficiency of secondary ions of the MCP 17. The distance L is a bit less than 10 cm, so that, the time of flight of the emitted hydrogen ions is, for instance, in the order of 300 ns. A typical time resolution of a MCP or a secondary electron multiplier is in the order of a few ns, so that it is apparent that the sufficient mass resolution in the hydrogen detection can be obtained by the presently used method according to the invention.

Figure 10:
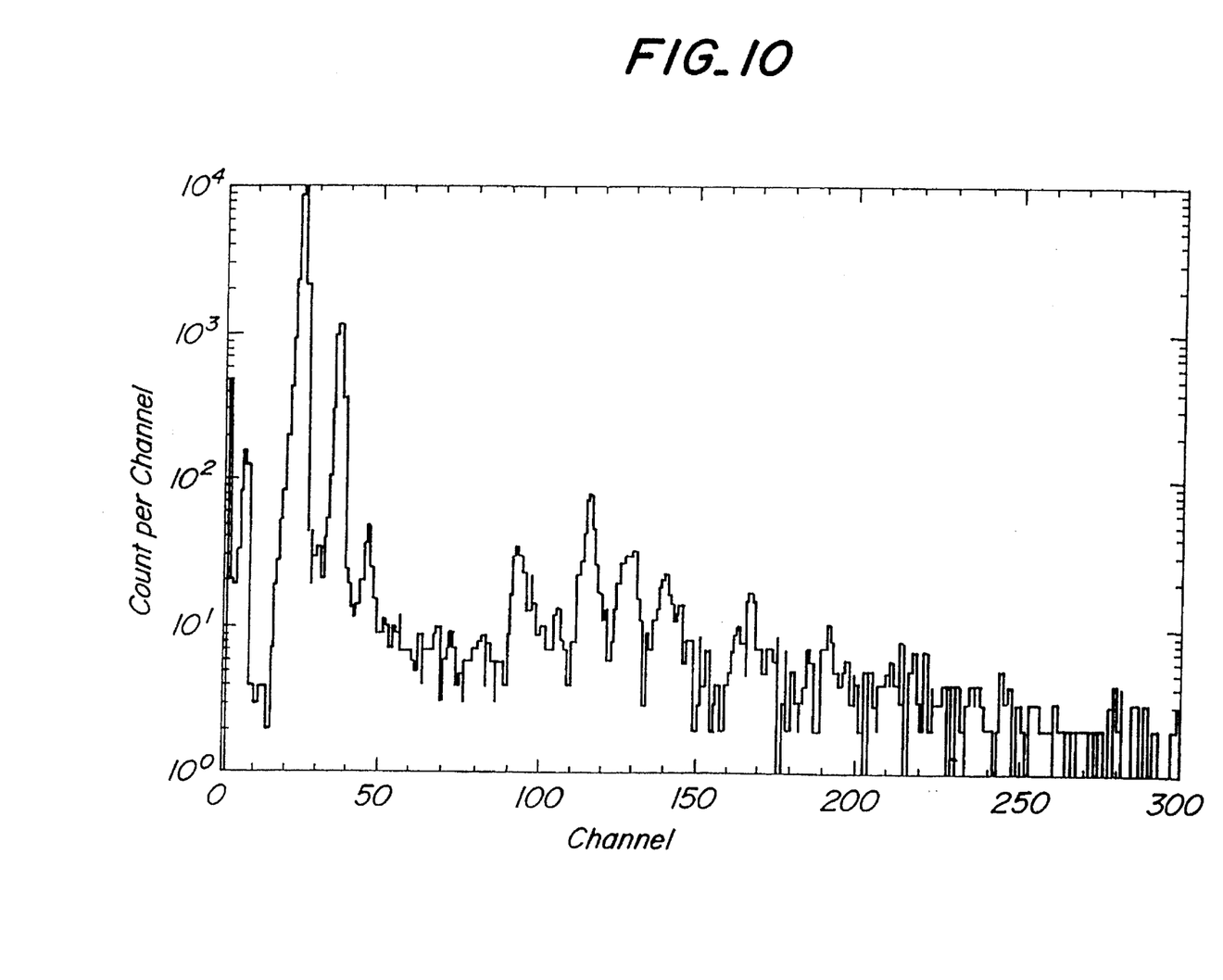
FIG. 10 is a diagram showing an example of the TOF spectrum for 500 eV Ar ion bombarding hydrogen-containing $C_{60}$.

Thus measured time of flight spectrum of the secondary ion for 500 eV $Ar^{12+}$ striking a $C60$ target is shown in FIG. 10. In this case, the yield of the hydrogen ion $H^+$ is seen to be three orders of magnitudes stronger than that of carbon ions $C^+$ or $C_2^+$, intrinsic species construction the target. So that, it has been confirmed that the efficiency of hydrogen ion detection on the basis of slow multiply-charged ions according to the present invention is extremely high.

EMBODIMENT

The interaction between a slow multiply-charged ion and a matter is noteworthy because of high potential energy held by this ion. The slow multiply-charged ion is neutralized with multiple electron transfer from the material surface upon the approach thereto. Thus emittable coulomb potential energy amounts to for instance to 4 keV in the case of $Ar^{14+}$. A mechanism to deposit such a large potential energy to the material is quite different from that to deposit a kinetic energy from a fast ion with low charge state. In the former case, large energy held by the ion is primarily given to the target surface. It can be anticipated from this feature that the atoms absorbed on the mass surface can be extremely efficiently dissociated, as confirmed by the following experiment.

Slow (0.3 keV) multiply-charged (q=4 to 16) argon ions extracted from the EBIS type ion source are irradiated on the target deposited with $C60$ thereon. Thus dissociated positive charge ions are detected with the time of flight (TOF) method, so as to measure the kind, the charge and the yield thereof. The yield of thus detected various carbon cluster ions increases as the charge state of the argon ion increases. Particularly, it could be found that the yield of hydrogen ions increases remarkably as the charge state increases such as the yield is proportional to $q^3$ to $q^5$.

Generally, the auger electron spectroscopy and the photoelectron spectroscopy cannot be used for the detection of hydrogen absorbed on the solid surface, so that other surface detecting methods have been investigated. However, any of them has insufficient efficiency and inferior quantitativity. In contrast therewith, the above experimental result suggests that the slow multiply-charged ion has an extremely excellent detection efficiency of hydrogen absorbed on the solid surface and hence an effective detecting method can be provided thereby.

The principle of the electron beam ion source (EBIS) used for the detection method according to the present invention will be hereinafter explained as follows.

As shown in FIG. 5, when an electron beam 27 passes through a cylindrical metal tube called as a drift tube 28, an electric potential shown in FIG. 7A is generated between the electron beam 27 and the drift tube 28. In FIG. 7A, examples of the radial potential distribution are shown for various positions of the electron beam 27. The gas introduced in the drift tube 28 is ionized by the electron beam 27 and, once ionized, attracted toward the electron beam. When the potential is deep enough, ions are bound in the radial direction as shown in FIG. 7B. Therefore, ions are successively bombarded by the electron beam. As a result, multiply-charged ions are generated by a step-by-step ionization such as Ions are bound strongly when the electron density is increased. The electron beam 27 is compressed into high density by an intense magnetic field in the axial direction of the drift tube 28 through the solenoid coil 29. As shown in FIG. 5, the cathode 22 is shielded from the magnetic field with the μ-metal 26A and the soft iron pipe 25A. As a result, the magnetic field can be abruptly raised as shown in FIG. 6A. This magnetic field distribution and an electrostatic lens effect between the cathode 22 and the anode 23 abruptly compress thermal electrons emitted from the cathode 22 in the radial direction. The electron beam starts to expand behind the μ-metal 26B and the soft iron pipe 25B due to the mutual coulomb repulsion because of the weak magnetic field as seen in FIG. 6A, and finally is collected by the electron collector 31.

The generated ion beam is not bound axially, and hence freely passes through the ionization region. For preventing this, as shown in FIG. 6B, the potentials at both ends of the drift tube 28 are raised higher by a several volt to a several tens volt with respect to the central region, so as to provide a potential barrier against ions, which traps ions also in the axial direction.

For mitigating such effects caused in the step of ionization progress as electron capture from residual gas and cancellation of spatial electric charge by the ionized residual gas as described later, it is required to keep the whole ion source in ultra high vacuum. The process of step-by-step ionization is largely enhanced if the density of electron beam is much increases, which also helps to reduce affects of residual gases.

There are two ways to extract ions from the ion source, i.e., a pulse mode and a continuous mode. The former is to keep the potential barrier high to completely confine ions for a determined time duration, and then the voltage applied on the barrier of the output side is lowered for a short time so as to get pulsed ions. So that this method has a merit that the intensity of multiply-charged ion beam is further increased.

On the other hand, the latter mode keeps the barrier very low which allow a part of multiply-charged ions to ooze out continuously. This method has a merit that the energy width of the ion beam is very narrow. The present invention adopted the latter method.

FIG. 3 shows the whole structure of EBIS type ion source used in the present invention, in which all of the following constituents are arranged in the vacuum chamber of 200 mm$\phi$ diameter and 500 mm length, which is evacuated through a turbo-molecule pump 34 with an evacuation speed of 300 L/sec.

(a) Solenoid Coil

It is required for attaining the ultra high vacuum to bake the aforesaid vacuum chamber at about 200° C., so that the solenoid coil is formed of copper wire of 0.7 mm diameter coated with high heat-resistant polyimideamide. The solenoid coil of 252 mm length, 48 mm$\phi$ inner diameter, and 100 mm$\phi$ outer diameter consists of three separated coils having total 13,000 turn winding. The solenoid coil is accommodated in a cylindrical liquid nitrogen filled chamber of 284 mm length, 38 mm$\phi$ inner diameter, 120 mm$\phi$ outer diameter, which is supplied liquid nitrogen from a container which is used also as a cryostat for improving high vacuum as shown in FIG. 4. Outside the solenoid coil 29, four iron bars 30 are provided as magnetic return yokes as shown in FIG. 3. The solenoid coil 29 is suspended by spokes 35 for thermal insulation. The spokes 35 is suspended loosely to allow them to shrink during liquid nitrogen cooling. The electrical resistance of the solenoid coil is 132.6 Ω at room temperature, and is 17.1 Ω at 77K. At the central portion, a magnetic field of 1.2 kG is generated at 77° K. with 50 W electric power and with the consumption rate of liquid nitrogen is 1.1 L/hour.

As to the solenoid coil, the following are required, (1) the generation of a uniform magnetic field
(2) the coincidence between the axis of the generated magnetic field and the central axis of the drift tube.

The former is required because the density of the electron beam and the radial electric potential relating thereto depend on the intensity of the generated magnetic field, while the latter is required because the radial electric potential in the electron beam is varied by the incoincidence there between, so as to prevent the unstability of the ionization region which directly affects the performance of the ion source.

(b) Electron Gun, Drift Tube and Others

The electron gun 24 and the electron collector 30 are magnetically shielded by μ-metals 26A, 26B and soft iron pipes 25A, 25B from the magnetic field of the solenoid coil 29. A cathode is made of Ni of 2 mm$\phi$ coated with BaO which is commercially available. A heater warms up the cathode indirectly with 2.1 W. An aperture of the anode 23 is 2 mm$\phi$ and an inner diameter of the drift tube 28 is 4 mm$\phi$. The electron collector 30 generates the heat of about 30 W and hence is cooled by liquid nitrogen.

(c) Cooling of Multiply-charged Ions

The kinetic energy of the ion increases with the increase of the charge state. On the other hand, residual gas consists mainly of light atoms, so that, ions of residual gas having small kinetic energy on the average cools ions of heavy atoms via collisions and, as a result, multiply-charged ions are further deeply trapped by the electron beam and ions of light atoms are heated up, as a result, are successively lost from the trapping region. When a gas consisting of heavy elements is introduced, the intensity of multiply-charged ion of the heavy elements mixed with a small amount of light residual gas is higher than that with no residual gas, because of the aforesaid reason. According to this effect, the strict condition on vacuum is somewhat mitigated, so that, the high quality of the EBIS type ion source can be maintained even at insufficient vacuolity.

(d) Measurement of Ion Beam

Figure 11:
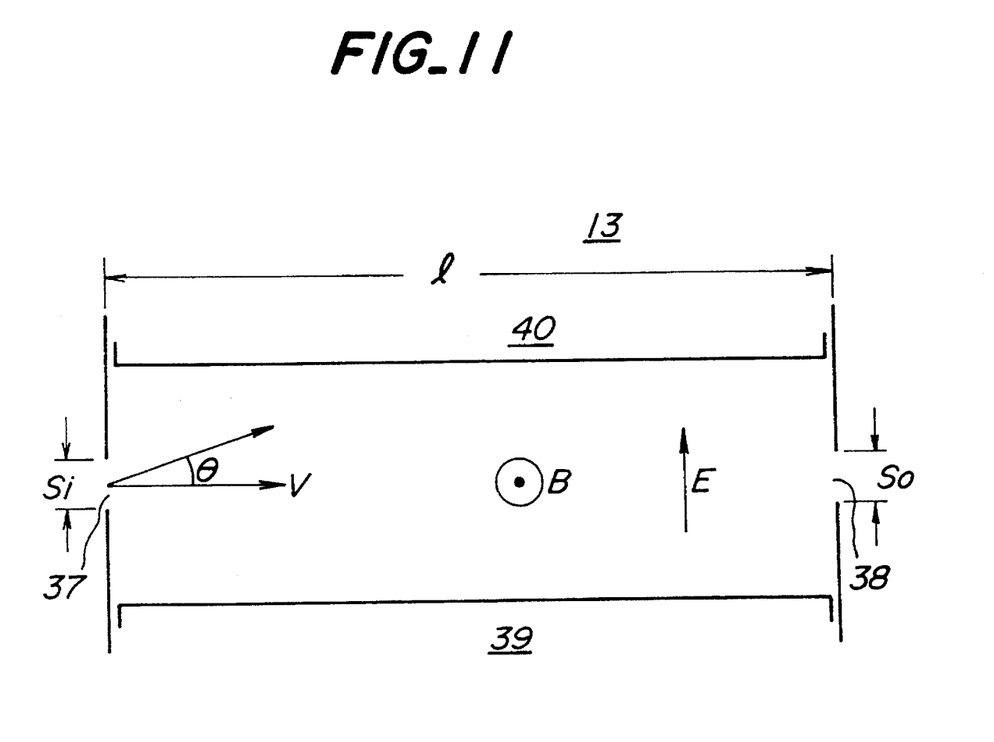
FIG. 11 is a diagram showing the principle of a Wien filter type mass analyzer (WF-MS) used in the embodiment of the present invention.

For sorting out kinds and charge states of ions extracted from the EBIS type ion source, a Wien filter type mass analyzer 13 is employed, wherein a uniform electric field is applied perpendicular to the direction of the ion beam and a magnetic field is applied to the ion beam in the direction perpendicular to the beam and the electric field in such a way that the force on the ion due to the magnetic field is antiparallel to the force due to the electric field. In this situation, only those ions, which satisfies the condition $v=E/B$ where v is the speed of ions, B and E are the magnetic and electric fields in the mass analyzer, respectively, can pass the analyzer.

In this conditions, $$m/qe = 2V_a H^2/E^2.$$

where e is the elementary electric charge, and $V_a$ is the acceleration voltage between the ion source and the mass analyzer. Further, if $$m/qe = LB^2/\pi E$$

and $V_a = LE/2\pi$ where L is the length of analyzing region, the point of the first order focusing hits the exit slit 38, i.e., all of those ions which are injected into the entrance slit 37 at a small injection angle θ, can pass through the exit slit 38. In this condition, the ultimate resolution is given by $$m/\Delta m \int 1/\pi \, (S_1 + S_0)$$

where $S_1$ and $S_0$ are widths of the entrance and exit slits, respectively.

Figure 12A:
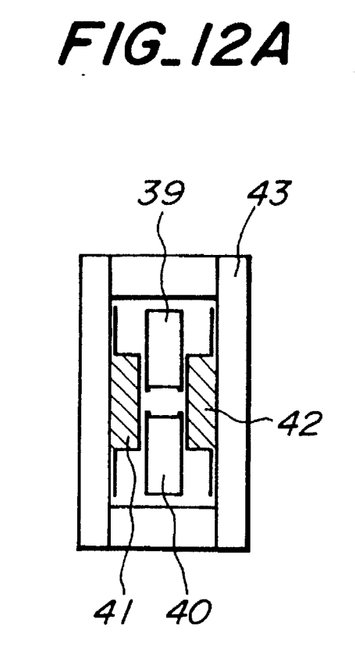
FIGS. 12A and 12B are diagrams showing traverse and longitudinal crosssections of the mass analyzer (WF-MS) as shown in FIG. 11, respectively.
Figure 12B:
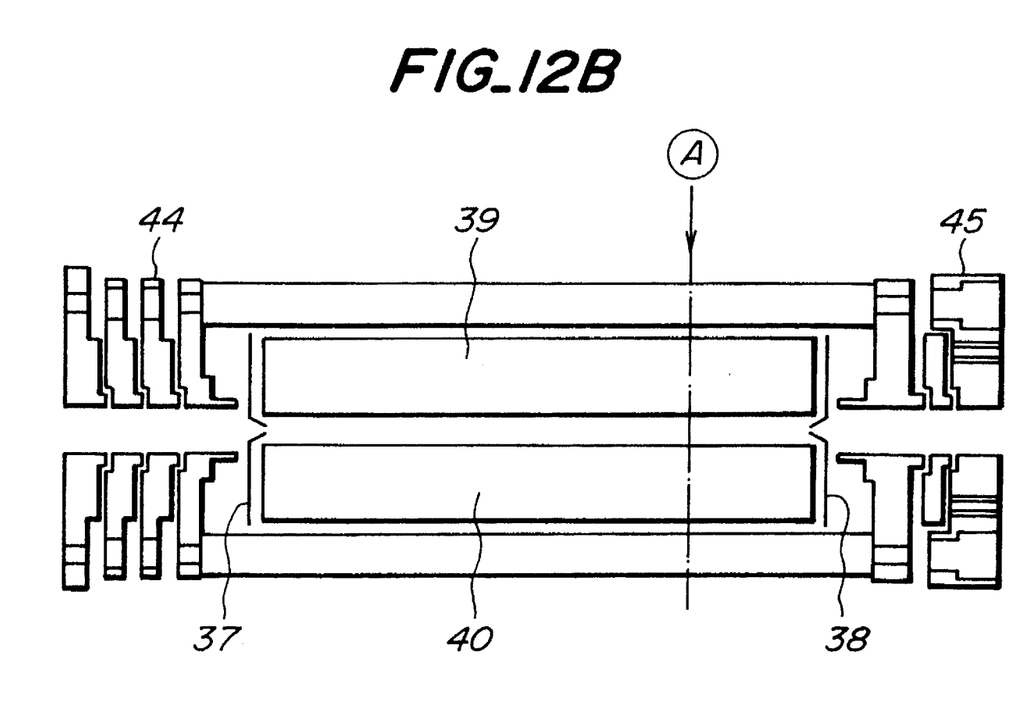

FIGS. 12A, B show a trial structure of the mass analyzer, in which the length of analyzing region is 90 mm, the width between electrodes is 5 mm and the maximum magnetic field of about 1,400 G is attained at the central portion employing a pair of permanent magnets.

Figure 13:
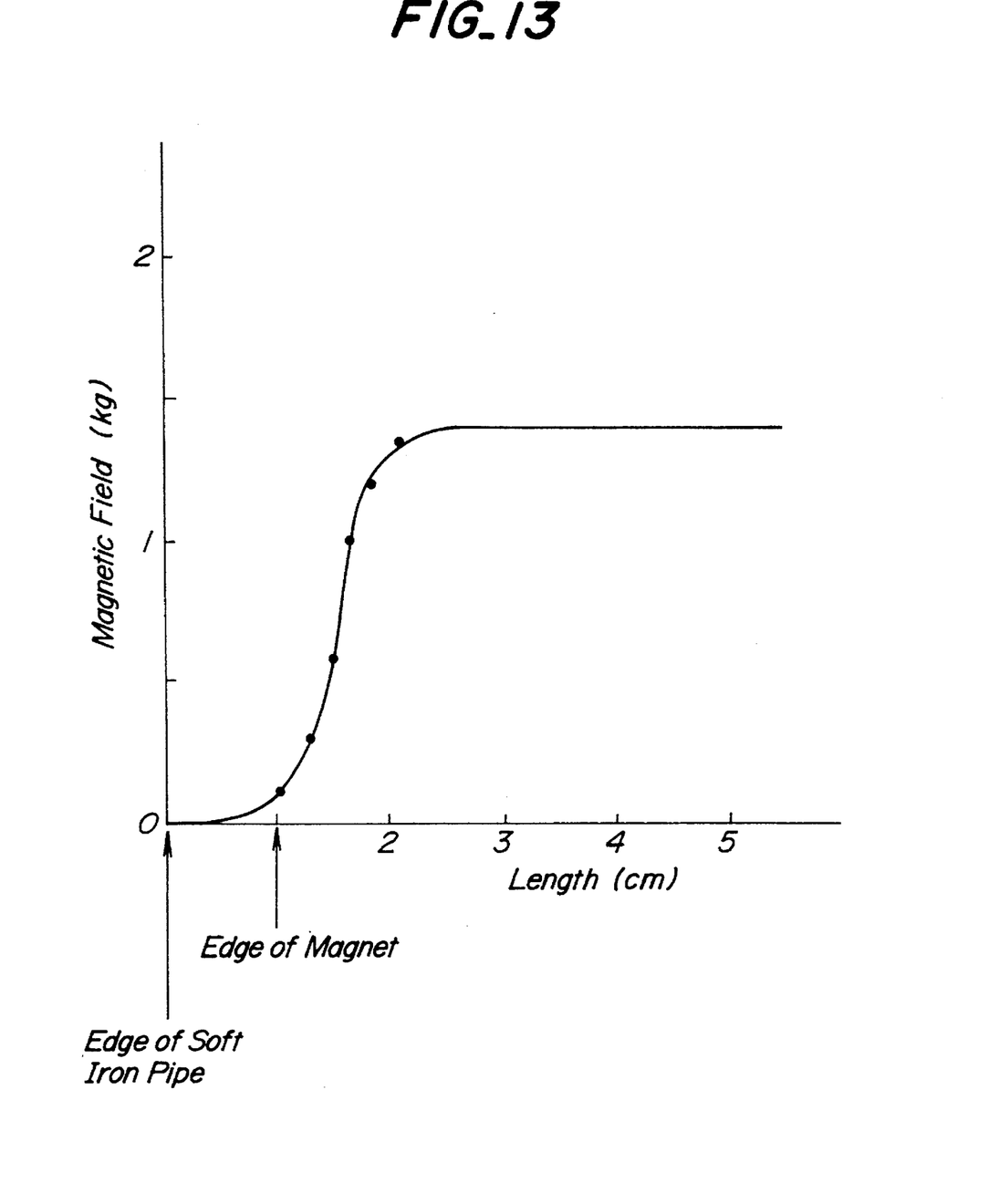
FIG. 13 is a diagram showing the magnetic field distribution around the edge of the mass analyzer (WF-MS) as shown in FIG. 11.

FIG. 13 shows the distribution of the magnetic field measured along the central axis of the mass analyzer. For the same entrance and exit slit widths of 0.5 mm, the ultimate resolution is calculated to be about 30. However, the strength of magnetic field B has been determined, so that, if m/q is set at a certain value, Va and E are of themselves determined. As a result, the resolution relating to ions having various values of m/q is deteriorated.

As is apparent from experimental data for 500 eV $Arq^+$ shown in FIG. 9, in the case of q=16 for example, one hydrogen ion is released from the surface and detected per ten injected ions. This means that, as for the hydrogen detection efficiency, the detection method according to the present invention has such a sensitivity as about one billion (109) times higher than that according to the conventional resonant nuclear reaction method. In addition, because particles having extremely low kinetic energy and extremely low intensity are employed, the so-called kinetic sputtering and the radiation damage within the target are negligibly small, so that the detection method of the present invention can be regarded as a remarkably excellent method for clarifying the hydrogen distribution on the first layer of the solid surface.

As is apparent from the above description, according to the present invention, on the basis of slow multiply-charged ions from an ion source for efficiently generating such ions like an electron beam ion source (EBIS) or an ECS ion source (ECSIS), the quantitative analysis of hydrogen on a solid surface can be compactly realized with extremely high efficiency. Further, damages caused on a target surface can be drastically reduced as compared with conventional methods, so that a remarkable industrial advantage can be obtained for largely improving the method of detection of this kind.

What is claimed is:

1. A method of ultra high sensitivity hydrogen detection based on slow multiply-charged ions comprising: arranging an EBIS type slow multiply-charged ion source for generating slow multiply-charged ions having a larger potential energy than kinetic energy, a Wien filter type mass analyzer, a deflector to produce a pulsed ion beam, an acceleration ring provided with apertures, lenses and a secondary ion detector, a mesh target provided on the acceleration ring and a secondary electron multiplier in order on a beam line for carrying ions from the ion source; detecting secondary ions generated upon the collision of slow multiply-charged ions with a target on a Cu mesh by accelerating toward the secondary ion detector; detecting secondary electron(s) on the secondary electron multiplier by repelling toward the mesh target thereof, and measuring the time difference between a secondary electron detection time on the secondary electron multiplier and a secondary ion detection time on the secondary ion detector, thereby effecting a quantitative analysis of hydrogen atoms on a solid surface of the mesh target.

2. A method of ultra high sensitivity hydrogen detection as claimed in claim 1, wherein the EBIS type slow multiply-charged ion source comprises an electron gun, a drift tube, a solenoid coil surrounding the drift tube, iron bars surrounding the solenoid coil and an electron collector provided outside the drift tube, an entrance and an exit of the drift tube are magnetically shielded, thereby generating an intense magnetic field in the axial direction of the drift tube by forming an electron beam with high density.

* * * * *